United States Patent [19]

Habermeier et al.

[11] 4,191,835
[45] Mar. 4, 1980

[54] BIS-ANTHRANILATES OF UREA DERIVATIVES

[75] Inventors: Jürgen Habermeier, Pfeffingen; Roland Moser, Basel, both of Switzerland

[73] Assignee: Ciba-Geigy Corporation, Ardsley, N.Y.

[21] Appl. No.: 966,425

[22] Filed: Dec. 4, 1978

[30] Foreign Application Priority Data

Apr. 27, 1978 [CH] Switzerland ................. 4587/78

[51] Int. Cl.² .................. C07C 101/54; C08G 59/54
[52] U.S. Cl. ........................ 560/49; 528/64; 528/68; 528/123; 528/341; 528/361; 528/365
[58] Field of Search ........................ 560/49

[56] References Cited

U.S. PATENT DOCUMENTS

| 3,817,940 | 6/1974 | Blahak et al. | 260/77.5 AM |
| 3,929,863 | 12/1975 | Blahak et al. | 560/50 |
| 4,007,239 | 2/1977 | Blahak et al. | 260/455 R |

FOREIGN PATENT DOCUMENTS

| 847680 | 2/1977 | Belgium | 560/49 |
| 847681 | 2/1977 | Belgium | 560/49 |
| 1073464 | 6/1967 | United Kingdom | 260/553 R |

OTHER PUBLICATIONS

Wong et al., J.A.C.S., 73, pp. 5557–5559 (1951).
Sherman Williams Technical Bulletin, 152 at p. 4.

Primary Examiner—Bernard Helfin
Assistant Examiner—G. T. Breitenstein
Attorney, Agent, or Firm—Joseph F. DiPrima

[57] ABSTRACT

Bis-anthranilates of the formula I

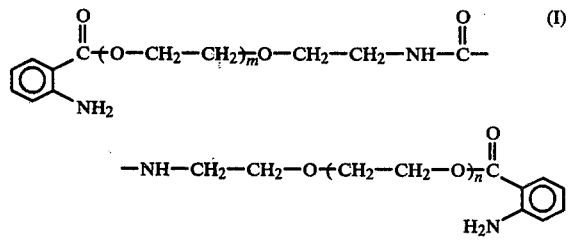

or mixtures thereof, in which, in the formula, m and n are each 0 or a number from 1 to 5, preferably a number from 1 to 3, and the sum of m and n must be at least 1, as novel chain extenders and crosslinking agents for the production of polyurethanes and polyurea resins. The compounds of the formula I are also suitable as curing agents for epoxide resins.

3 Claims, No Drawings

BIS-ANTHRANILATES OF UREA DERIVATIVES

The present invention relates to bis-anthranilates of polyoxyethylated urea, processes for their preparation and their use as chain extenders and crosslinking agents in the production of polyurethanes and polyurea resins or as curing agents for epoxide resins.

4,4'-Methylene-bis-(o-chloroaniline) (MOCA) has for a long time been one of the best chain extenders and crosslinking agents introduced into polyurethane and polyurea technology, since MOCA, especially in the production of polyurethane elastomers of flexible foams, has advantageous processing characteristics in respect of the reactivity and, moreover, imparts outstanding mechanical properties to the crosslinked polymers. As is known, however, there is a suspicion that MOCA may be carcinogenic (cf. "Elastomerics", March 1977, page 37) and there has been no lack of attempts to replace MOCA by crosslinking agents which are equivalent in respect of the very advantageous processing characteristics and end characteristics of the polymers.

In Technical Bulletin 152 of the "Sherwin-Williams Company" (USA), bis-anthranilates of linear aliphatic diols are mentioned. In "Elastomerics", March 1977, page 37 et seq., 4,4'-methylene-bis-anthranilates are proposed as a replacement for MOCA. Furthermore, in the two Belgian Patent Specifications Nos. 847,680 and 847,681, bis-anthranilates of diols containing a N,N-heterocyclic radical, for example 1,3-di-(2'-hydroxyethyl)benzimidazolone and 1,3-di-(2'-hydroxyethyl)-5,5-dimethylhydantoin, are disclosed as chain lengtheners for polyurethanes.

It has now been found that when bis-anthranilates of polyoxyethylated urea, for example N,N'-bis(β-hydroxyethoxyethyl)-urea, are used as chain extenders and crosslinking agents in urethane and urea formulations, elastomers with advantageous mechanical properties are obtained. The novel bis-anthranilates also have the advantage that they can be processed easily at room temperature in the urethane and urea formulations and are readily soluble in these formulations and, moreover, are suitable for cold curing.

The invention thus relates to novel bis-anthranilates of the formula I

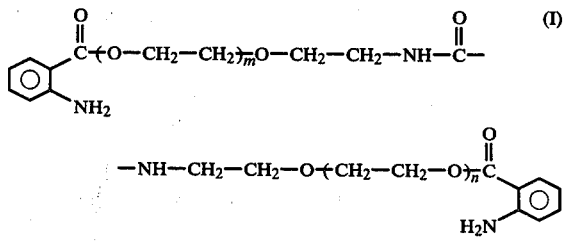

or mixtures thereof, in which, in the formula, m and n are each 0 or a number from 1 to 5, preferably a number from 1 to 3, and the sum of m and n must be at least 1. The compound of the formula I in which m and n are each 1 is of particular interest.

The compounds of the formula I can be prepared by reacting 1 mol of a polyoxyethylated urea of the formula II

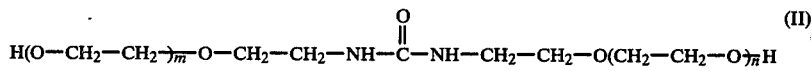

or mixtures thereof, in which m and n are as defined in formula I, with 1.8 to 2.5 mols of isatoic anhydride, preferably in the presence of a basic catalyst, to give compounds of the formula I.

The starting compounds used in this process are preferably compounds of the formula II in which m and n are each a number of 1 to 3; in particular N,N'-bis-(β-hydroxyethoxyethyl)-urea is employed.

In a preferred embodiment, the starting compounds are used in stoichiometric amounts, i.e. 1 mol of the polyoxyethylated urea of the formula II is employed per 2 mols of isatoic anhydride.

The pure compounds of the formula II have not previously been described in the literature and can be prepared using the process described in U.S. Pat. No. 2,379,261, by reacting 1 mol of urea with 2 mols of a poly-(oxyethylene)-glycolamine of the formula III

with the elimination of 2 mols of ammonia, to give compounds of the formula II. In this process, the poly-(oxyethylene)-glycolamine is preferably employed in molar excess and this excess is removed from the reaction mixture by distillation after the reaction has taken place.

Another process for the preparation of compounds of the formula II comprises subjecting the N,N'-bis-(β-hydroxyethyl)-urea, prepared in a first stage, to an addition reaction, in a second stage, with m+n mols of ethylene oxide in the presence of a catalyst. Compounds of the formula II are obtained in the form of a mixture of oligomers by this process, as is shown by Example A below.

The N,N'-bis-(β-hydroxyethyl)-urea prepared in the first stage is known and can be obtained by the process described in Example 1 of U.S. Pat. No. 2,379,261, by reacting urea with ethanolamine with the elimination of ammonia. Bis-(hydroxyethyl)-urea can also be prepared from ethanolamine and COS in good yield according to German Auslegeschrift 1,468,398.

The preparation of the compounds of the formula I preferably takes place in the presence of an organic solvent or solvent mixture. Suitable solvents are, in particular, the aprotic solvents, such as dioxan, chloroform, toluene, dimethylformamide and dimethylacetamide.

The reaction temperature for the preparation of the compounds of the formula I can be from 30° to 160° C. Preferably, the reaction is carried out in the temperature range of 50° to 130° C.

Appropriately, the conversion reaction is catalysed by bases, and alcoholates, including those of the starting diols, alkali metal hydroxides or alkaline earth metal hydroxides, tertiary amines and ammonium bases or other substances having a basic action can be used. Frequently, basic impurities in the starting materials also suffice. Catalysts can be used in amounts of 0.01 to 10 mol %, based on the amount of isatoic anhydride employed.

Another process for the preparation of the compounds of the formula I comprises esterifying 1 mol of a bis-(hydroxyalkyl)-urea of the formula II with 2 mols of o-nitrobenzoic acid and then reducing the nitro groups in a known manner to the amino groups.

The compounds of the formula I can also be prepared by a transesterification process, by transesterifying the bis-(hydroxyalkyl)-ureas of the formula II with anthranilates, preferably alkyl anthranilates having 1 to 4 C atoms in the alkyl group, the alcohol formed during the reaction being distilled off.

The compounds, according to the invention, of the formula I are viscous to glassy solid substances at room temperature. The solid products have low softening points (30°–80° C.). The novel compounds are readily soluble in many organic solvents, such as dioxan, toluene, benzene, dichlorobenzene and dimethylformamide. Furthermore, the novel compounds have good solubility at room temperature in higher-molecular diols, diolether compounds and short-chain polyesters containing hydroxyl groups.

As mentioned initially, the compounds according to the invention are a suitable replacement for 4,4′-methylene-bis-(o-chloroaniline). They can therefore be used in an analogous manner. In particular, the compounds according to the invention are suitable as chain extenders in polyurethanes and as crosslinking agents for the production of polyurea resins and can advantageously also be employed for cold curing. Moreover, the compounds according to the invention can be used as curing agents for epoxide resins.

PREPARATION OF THE STARTING COMPOUNDS

Example A

A 1 liter autoclave is charged at room temperature with 300 ml of dioxan, 5.0 g of sodium hydroxide powder, 148.2 g (1.0 mol) of N,N′-bis-($\beta$-hydroxyethyl)-urea and 176.2 g (4.0 mols) of ethylene oxide. The mixture is heated to 130°–150° C. and the reaction starts exothermically and has ended after a short time (45 minutes). The mixture is cooled to room temperature, neutralised with 8 ml of acetic acid and concentrated completely. The residue is then dried to constant weight at 125° C. and 26 Pa. This yields 302.4 g of a yellowish, clear liquid product. The H-NMR spectrum (60 Mc) and combustion analysis show that the product has the structural formula given below. After the OH groups have been converted to O—Si(CH$_3$)$_3$ groups by means of conventional silylation reagents, the oligomeric distribution can be determined by means of gas chromatography and the results of this are given below:

H—(O—CH$_2$—CH$_2$)$_m$O—CH$_2$—CH$_2$—NH
—CO—NH—CH$_2$—CH$_2$—O—CH$_2$—(CH$_2$—O)$_n$H

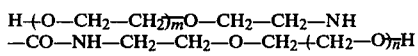

m+n=1: 29 mol %
m+n=2: 19.5 mol %
m+n=3: 23 mol %
m+n=4: 10.0 mol %
m+n=5: 9.5 mol %
m+n=6: 6.5 mol %
m+n=7: 2 mol %

Example B

N,N′-Bis-($\beta$-hydroxyethoxyethyl)-urea 46.05 g (1 mol) of industrially produced urea are mixed with 420 g (4 mols) of diethyleneglycolamine (=$\beta$-aminoethoxyethanol) in a 1 liter glass apparatus with a reflux condenser, a gas outlet, a stirrer, a thermometer and external heating, and the mixture is warmed to 110° C., with stirring, whereupon a clear solution forms. The solution is then stirred for 6 hours at 125°–130° C. and the reaction proceeds with the elimination of ammonia. The excess diethyleneglycolamine is then distilled off at 130° C. under 65 Pa. 208 g (99% of theory) of diethyleneglycolamine are recovered. The product is obtained in 86% yield (203.5 g) in the form of a colourless, viscous liquid.

Analysis by gas chromatography (GC) after silylation of the —OH groups (with "Trisil BSA" from Pierce) shows that this product is 98.9% pure and contains a single impurity (1.1%). Both the H-NMR spectrum (60 Mc) and the combustion analysis are in accord with the structure given below. The following values were found for C$_9$H$_{20}$N$_2$O$_5$

| found: | calculated |
|---|---|
| 45.65% C | 45.75% C |
| 8.60% H | 8.53% H |
| 11.90% N | 11.65% N |

$$\text{HO—CH}_2\text{—CH}_2\text{—O—CH}_2\text{—CH}_2\text{—NH—}\overset{\overset{\text{O}}{\|}}{\text{C}}\text{—NH—CH}_2\text{—CH}_2\text{—O—CH}_2\text{—CH}_2\text{—OH}$$

The GC analysis (100° C.; column SP 2100, carrier He) also shows that the recovered diethyleneglycolamine (208 g) has a purity of 99.4% and can be used direct for further batches.

PREPARATION EXAMPLES

Example 1

Bis-anthranilate of polyoxyethylurea according to Example A 281 g (=0.996 mol) of the mixture of oligomers prepared according to Example A are dissolved in 140 ml of dioxan at 65° C.; 0.3 g of potassium hydroxide powder and 120.2 g of isatoic anhydride are added, with stirring. The reaction starts immediately with the evolution of CO$_2$ and a clear, pale brown solution forms. After one hour, the solution is warmed to 80° C. and 0.3 g of potassium hydroxide and 120.2 g of isatoic anhydride are added, and after a further 90 minutes, a further 0.2 g of potassium hydroxide and 120.2 g of isatoic anhydride (total 360.6 g=1.992 mols) are added. The reaction mixture is then stirred for a further 3.5 hours at 85° C. It is concentrated completely at 100° C./260 Pa, the product is dissolved in 250 ml of chloroform and the solution is washed twice with 100 ml of NH$_3$ solution (10%) and twice with 100 ml of water. The organic phase is concentrated completely and the residue is dried to constant weight at 120° C./65 Pa.

This yields 449 g (=86.9% of theory) of a bisanthranilate which is highly viscous at room temperature. The H-NMR spectrum (60 Mc) and combustion analysis are in accord with the structure given below. The following values are obtained for $C_{25}H_{34}N_4O_8$ (corresponding to average values for the distribution of m and n):

USE EXAMPLES

Examples I and II

A liquid isocyanate prepolymer which is obtained from toluylene diisocyanate and polytetramethylene glycol and has an isocyanate content of 1.5 equivalents/kg and a viscosity of about 10,000 mPa.s at 25° C.

| found: | calculated: |
| --- | --- |
| 6.69% H | 6.61% H |
| 10.14% N | 10.80% N |

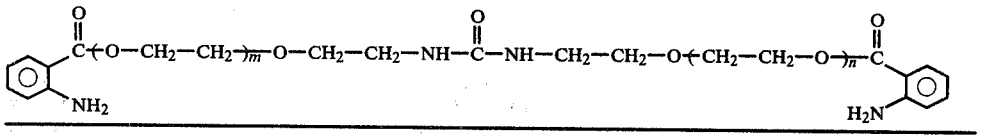

m+n correspond to the values in Example A.

Example 2

N,N'-Bis-(anthranoyloxyethoxyethyl)-urea 135.5 g (0.574 mol) of the N,N'-bis-(β-hydroxyethoxyethyl)-urea prepared according to Example B are dissolved in 650 ml of toluene at 80° C. 0.5 g of potassium hydroxide powder is added with stirring and 68.7 g of isatoic anhydride are added. The esterification starts immediately with the evolution of $CO_2$. After 90 hours, a further 0.5 g of potassium hydroxide and 68.7 g of isatoic anhydride are added. After a further 90 minutes, a further 0.5 g of potassium hydroxide and 68.7 g of isatoic anhydride (total thus 206 g=1.263 mols) are added. The reaction mixture is then stirred for a further 120 minutes at 110° C. and is concentrated completely at 100°–120° C./98.8–1.95 kPa. A clear, pale brown, glassy product, which softens at about 40° C., is obtained in quantitative yield (273 g). The thin layer chromatogram (solvent:cyclohexane/acetone, 1:1) shows that the desired product is contaminated only slightly by by-products.

For purification, the product is dissolved in 250 ml of chloroform and the solution is twice extracted by shaking with 150 ml of 10% $NH_4OH$, washed twice with 150 ml of water and concentrated completely. After drying at 130° C./52 Pa, 257 g of a clear, pale yellow product are obtained, the H-NMR spectrum (60 Mc) and combustion analysis of which are in accord with the structure given below. The following values were obtained for $C_{23}H_{30}N_4O_7$ (available commercially under the name "Adipren L-167") was mixed with the bis-anthranilates prepared in Examples 1 and 2.

The constituents of these mixtures were in each case mixed in the ratios and under the processing conditions indicated in Table 1 and 2. The following methods were used to determine the reactivity of the mixtures and their mechanical properties after complete curing.

Determination of the reactivity

The reactivity was determined by measuring the gel times on thermostat-controlled hotplates which were set at 60°, 80°, 100°, 120° and 140° C.

Determination of the mechanical properties of the elastomers

After intimate mixing under the particular conditions indicated in Table 1, the resin/crosslinking agent mixtures listed in Table 1 and 2 were freed in vacuo from the air stirred in during mixing and then poured into aluminium moulds, pre-treated with mould-release agents, to produce sheets with dimensions of 135×135×4 mm and 135×135×1 mm and were completely cured under the conditions indicated in Table 2.

Test pieces which correspond to DIN 53,455, No. 4 were stamped out from the 4 mm thick sheets using a punch and the tests to determine the tensile strength and elongation at break were carried out on these. The remainder of the 4 mm sheet was used for determining the Shore A hardness (DIN 53,505) and the impact resilience according to DIN 53,485.

Shaped pieces for determining the tear propagation resistance according to DIN 53,363 were cut out from the 1 mm thick sheet.

| found: | calculated: |
| --- | --- |
| 58.30% C | 58.22% C |
| 6.40% H | 6.37% H |
| 11.80% N | 11.81% N |

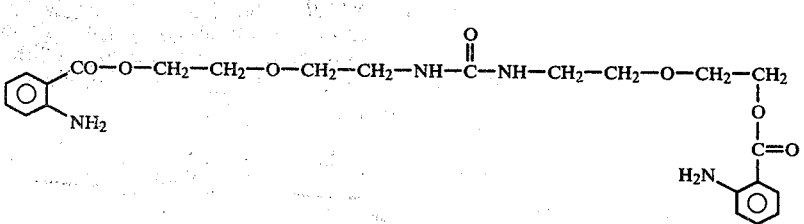

Table 1

Processing conditions and reactivity

| Use example | I | II | Comparison Example a | Comparison Example b |
|---|---|---|---|---|
| Bis-anthranilate (crosslinking agent) | according to Example 1 | according to Example 2 | Bis-anthranilate of neopentylglycol* | MOCA |
| Appearance | brown, very highly viscous liquid | brown, very highly viscous liquid | dark brown, highly viscous mass | brownish powder |
| Viscosity in mPa.s | 60° C. = 6300  80° C. = 680 | 60° C. = 27000  80° C. = 1850 | 60° C. = 1875 | (melting point: 120° C.) |
| Parts of crosslinking agent per 100 parts of prepolymer | 31.1 | 32.0 | 25.1 | 16.0 |
| Processing conditions | Prepolymer and crosslinking agent homogenised at 60° C. | Prepolymer and crosslinking agent homogenised at 70° C. | Prepolymer and crosslinking agent homogenised at 80° C. | Prepolymer warmed to 80° C. and MOCA heated to 120° C. then mixed in |
| Gel time at 60° C. | 1420 | 2415 | | |
| (minutes) 80° C. | 40 | 1436 | | 34 |
| 100° C. | 27 | 55 | 1442 | 7 |
| 120° C. | 10.10 | 29 | 33 | 4 |
| 140° C. | 7.20 | 11.30 | 18 | 3 |

*Compound according to German Auslegeschrift 2,040,644

Table 2

End characteristics after crosslinking

| Use example | I | II | Comparison Example a | Comparison Example b |
|---|---|---|---|---|
| Crosslinking agent used | according to Example 1 | according to Example 2 | Bis-anthranilate of neopentyl-glycol* | MOCA |
| Crosslinking conditons (hours/°C.) | | 6/120 | | |
| Appearance of the elastomer | transparent pale brown | transparent pale yellow | transparent brown | yellow, opaque |
| Shore A hardness (units) | 57 | 68 | 61 | 92 |
| Impact resilience (%) | 9 | 16 | 8 | 26 |
| Tensile strength (N/mm²) | 19.2 | 41 | 17.8 | 42 |
| Elongation at break (%) | 528 | 525 | 640 | 333 |
| Tear propagation resistance (N/mm) | 17 | 36 | 27 | 100 |

*Compond according to German Auslegeschrift 2,040,644

Examples III and IV

A liquid, unmodified epoxide resin based on bisphenol A with an epoxide content of 5.3 equivalents/kg and a viscosity of 10800 mPa.s at 25° C. was mixed in equivalent ratios with the bis-anthranilates prepared in Examples 1 and 2 and the mixtures were melted together. 4 g amounts of the mixtures thus obtained were poured into small aluminium dishes about 5 cm in diameter. The glass transition temperatures of the moulded material obtained after complete curing was determined using a Thermoanalyzer (type TA 2000 from Mettler, Greifensee, Switzerland).

In order to test the adhesive characteristics, the mixtures prepared from the bis-anthranilates according to the invention were applied, whilst still in the uncrosslinked state (immediately after the curing agent had been dissolved in the resin) to the ends of aluminium (Anticorodal B) test strips which had dimensions of 170×25×1.5 mm and had previously been roughened by grinding and degreased by washing with acetone. In each case two of these test strips were so adjusted with the aid of a gauge that the ends coated with this resin/curing agent mixture overlapped by 12 mm. After fixing with a clamp, the adhesive bond was cured and after cooling the clamp was removed and the tensile shear strength was then tested in a tensile test according to DIN 53,183.

A further portion of the resin/curing agent system was applied to a glass plate and completely cured in an oven in accordance with the data in Table 3. The chemical resistance of the film thus obtained was determined, the procedure being as follows: one drop of each of the particular chemicals was left on the film for 1 hour. The chemicals were then wiped off and the surface of the film graded visually, grade 1 being given for no visible attack, grade 2 for slight attack on the surface of the film, grade 3 for severe attack on the film and grade 4 for complete destruction of the film.

Table 3

| Example | | III | IV |
|---|---|---|---|
| Bis-anthranilate (curing agent) | according to Example | I | 2 |
| | Amount (parts | 69.9 | 64.1 |

Table 3-continued

| Example | III | IV |
|---|---|---|
| by weight) per 100 parts by weight of epoxide resin | | |
| Curing conditions (hours/°C.) | 4/80 and 8/140 | |
| Appearance | brown, transparent moulded material | yellow, transparent moulded material |
| Glass transition temperature (°C.) | 80 | 92 |
| Tensile shear strength (N/mm²) | 26 | 22 |
| Appearance of the film | scratch resistant, pale brown film | scratch resistant, virtually colourless film |
| Chemical stability towards: | | |
| 5N H$_2$SO$_4$ | 1 | 1 |
| 5N NaOH | 1 | 1 |
| H$_2$O | 1 | 1 |
| Cl-benzene | 2 | 2 |
| Acetone | 2 | 2 |

What is claimed is:

1. A bis-anthranilate of the formula I

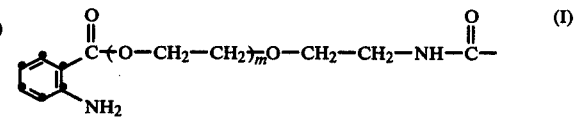
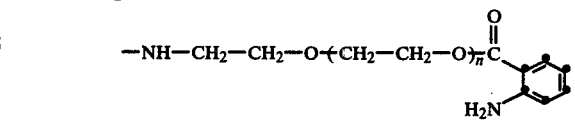

or a mixture of such bis-anthranilates, in which, in the formula, m and n are each 0 or a number from 1 to 5 and the sum of m and n must be at least 1.

2. A diester according to claim 1, in which m and n in the formula I are each a number from 1 to 3.

3. N,N'-Bis-(anthranoyloxyethoxyethyl)-urea as a compound of the formula I according to claim 1.

* * * * *